(12) United States Patent
Mase et al.

(10) Patent No.: US 7,381,855 B2
(45) Date of Patent: Jun. 3, 2008

(54) PROCESS FOR PRODUCING ADAMANTANE

(75) Inventors: Jun Mase, Ichihara (JP); Shinji Miyamoto, Ichihara (JP); Akio Kojima, Ichihara (JP); Masao Saito, Ichihara (JP); Toshiaki Kusaba, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 10/590,995

(22) PCT Filed: Feb. 28, 2005

(86) PCT No.: PCT/JP2005/003288

§ 371 (c)(1),
(2), (4) Date: Aug. 29, 2006

(87) PCT Pub. No.: WO2005/082817

PCT Pub. Date: Sep. 9, 2005

(65) Prior Publication Data

US 2007/0173678 A1    Jul. 26, 2007

(30) Foreign Application Priority Data

Mar. 1, 2004   (JP) ............................. 2004-056395

(51) Int. Cl.
*C07C 13/28* (2006.01)
*C07C 7/14* (2006.01)
(52) U.S. Cl. ...................................... 585/352; 585/812
(58) Field of Classification Search ................ 585/352, 585/812
See application file for complete search history.

(56) References Cited

U.S. PATENT DOCUMENTS 3,944,626 A * 3/1976 Honna et al. ................ 585/352
2006/0111596 A1   5/2006 Mase et al.

FOREIGN PATENT DOCUMENTS

| JP | 2004 51484 | 2/2004 |
| JP | 2004 59510 | 2/2004 |
| JP | 2004 59511 | 2/2004 |

OTHER PUBLICATIONS

U.S. Appl. No. 10/590,995, filed Aug. 29, 2006, Mase et al.
U.S. Appl. No. 10/582,607, filed Jun. 12, 2006, Kojima et al.

* cited by examiner

*Primary Examiner*—Thuan Dinh Dang
(74) *Attorney, Agent, or Firm*—Oblon, Spivak, McClelland, Maier & Neustadt, P.C.

(57) ABSTRACT

An industrially advantageous process for producing adamantane by which high-purity adamantane reduced in coloration is efficiently produced while minimizing the loss. The process, which is for producing adamantane by isomerizing trimethylenenorbornane, includes (A) a reaction step of isomerizing the starting material, (B) a concentration step of concentrating the adamantane contained in the resultant liquid reaction mixture, (C) a crystallization step of precipitating the concentrated adamantane, (D) a solid-liquid separation step of separating the adamantane crystals from the slurry resulting from the crystallization, (E) a washing step of washing the isolated adamantane crystals, and (F) a drying step of drying the adamantane crystals washed, characterized in that the mass ratio of the endo-trimethylenenorbornane to the adamantane each contained in the materials to be subjected to the crystallization step (C) (endo-trimethylenenorbornane/adamantane) is 0.25 or lower.

10 Claims, No Drawings

PROCESS FOR PRODUCING ADAMANTANE

TECHNICAL FIELD

The present invention relates to a process for producing adamantane. More specifically, the present invention relates to an industrially advantageous process for producing adamantane involving the use of a solid catalyst which eliminates the need for a troublesome operation such as waste liquid disposal and by which high-purity adamantane reduced in coloration is efficiently produced while minimizing the loss.

BACKGROUND ART

Adamantane has a structure in which four cyclohexane rings are bound to one another in a cage fashion, and is a compound having high symmetry and stability. Also, adamantane exhibits a specific function. Accordingly, adamantane is known to be useful as, for example, a lubricant, a starting material for an agricultural chemical or for a drug, or a starting material for a high functionally industrial material because adamantane shows a specific function.

Adamantane is obtained by isomerizing trimethylenenorbornane (TMN), which is obtained by hydrogenating dicyclopentadiene (DCPD), by using a catalyst. In addition, aluminum chloride is industrially used as the catalyst.

In addition, a known example of a solid catalyst is one obtained by causing zeolite subjected to cation exchange to carry an active metal such as platinum, rhenium, nickel, or cobalt by means of an impregnation method (see, for example, Patent Document 1).

When adamantane is produced by using aluminum chloride as a catalyst, in addition a large amount of the catalyst must be used, the catalyst cannot be recycled because the catalyst forms a complex with a heavy component during a reaction. Therefore, when the method is employed, a large amount of waste aluminum is produced. The disposal of waste aluminum is responsible for the problem of environmental pollution.

Furthermore, when aluminum chloride is used, there arises the following problem: produced adamantane is colored, so a decolorization step by using recrystallization, activated carbon, and the like is needed, and hence a subsequent treatment step vexatiously becomes complicated.

On the other hand, a process for producing adamantane involving the use of a catalyst obtained by causing zeolite subjected to cation exchange to carry an active metal such as platinum, rhenium, nickel, or cobalt by means of an impregnation method results in a low yield unless hydrogen chloride is made to coexist (TMN conversion ratio of 79.5%, adamantane selectivity of 10.1%, adamantane yield of 8.0%). Therefore, hydrogen chloride is indispensable to the process, and hence the process involves, for example, a problem in that an expensive device made of a corrosion-resistant material must be used owing to the strong corrosivity of hydrogen chloride.

In view of the foregoing, the inventors of the present invention have made studies with a view to coping with the above-mentioned problem, and have found an effective process for producing adamantane involving the use of not hydrogen chloride but a metal-carrying solid acid catalyst. In the process, an isomerization catalyst and how to use the catalyst in a reaction field have been proposed, but no industrial technique for producing adamantane including separation and purification treatments for produced adamantane has been disclosed.

Patent Document 1: JP-B-52-2906

DISCLOSURE OF THE INVENTION

Problems to be Solved by the Invention

An object of the present invention is to provide an industrially advantageous process for producing adamantane by which high-purity adamantane reduced in coloration is efficiently produced while minimizing the loss under such circumstances.

Means For Solving The Problems

The inventors of the present invention have made extensive studies with a view to solving the above problems. As a result, they have found that the above object can be achieved by: subjecting a liquid reaction mixture in which trimethylenenorbornane is isomerized to a specific step; and specifying the amount of endo-trimethylenenorbornane in a material to be subjected to a crystallization step. The present invention has been completed on the basis of such finding.

That is, the present invention provides the producing processes mentioned below:

1. A process for producing adamantane by isomerizing trimethylenenorbornane, the process including (A) a reaction step of isomerizing a starting material, (B) a concentration step of concentrating adamantane contained in the resultant liquid reaction mixture, (C) a crystallization step of precipitating the concentrated adamantane, (D) a solid-liquid separation step of separating adamantane crystals from slurry resulting from the crystallization, (E) a washing step of washing the isolated adamantane crystals, and (F) a drying step of drying the adamantane crystals washed, characterized in that a mass ratio of endo-trimethylenenorbornane to adamantane each contained in materials to be subjected to the crystallization step (C) (endo-trimethylenenorbornane/adamantane) is 0.25 or lower; and 2. A process for producing adamantane according to the above item 1, in which a solid catalyst is used in the reaction step of isomerizing the starting material is isomerized.

Effect Of The Invention

According to the present invention, there can be provided an industrially advantageous process for producing adamantane by which high-purity adamantane reduced in coloration is efficiently produced while minimizing the loss.

BEST MODE FOR CARRYING OUT THE INVENTION

A process for producing adamantane of the present invention includes the following respective steps: (A) a reaction step, (B) a concentration step, (C) a crystallization step, (D) a solid-liquid separation step, (E) a washing step, and (F) a drying step.

Next, each step will be described.

(A) Reaction Step

The reaction step is a step of producing adamantane by isomerizing trimethylenenorbornane (which may hereinafter be abbreviated as "TMN") according to a batch mode or a continuous mode.

Trimethylenenorbornane [tetrahydrodicyclopentadiene] can be easily obtained by hydrogenating dicyclopentadiene by using a catalyst for hydrogenation. The catalyst for hydrogenation to be used at this time is not particularly limited as long as it is a catalyst having hydrogenation activity, and preferable examples of the catalyst include Raney nickel and platinum.

In addition, the form of a hydrogenation reactor is not particularly limited. For example, a so-called fixed bed continuous reactor which is filled with a catalyst and is continuously supplied with a starting material can be used, but a reactor that can be used is not limited to this. A reactor of any form which is of an ordinary solid-liquid contact type or solid-gas contact type can be used irrespective of whether the reactor follows a continuous mode or a batch mode.

Dicyclopentadiene may be directly supplied, or may be supplied together with a solvent. At this time, the ratio of the solvent is ordinarily about 0 to 10 parts by mass, or preferably 0 to 3 parts by mass with respect to 1 part by mass of dicyclopentadiene.

In addition, the hydrogenation reaction is an exothermic reaction, and directly supplying a reaction product obtained here to an isomerization step can minimize energy for providing a temperature needed for an isomerization reaction.

Conditions for the hydrogenation reaction include: a reaction temperature of ordinarily about 0 to 500° C., or preferably 50 to 200° C.; a pressure of ordinarily normal pressure to about 10 MPa, or preferably 1 to 5 MPa; and a hydrogen/starting material compound molar ratio of ordinarily 2 or higher.

A solid catalyst to be used in the isomerization reaction is not particularly limited; provided that a solid acid catalyst, in particular, a metal-carrying solid acid catalyst is preferable, and aluminum chloride can also be used. Suitable examples of metal species in the metal-carrying solid acid catalyst include metals belonging to Groups 8 to 10 of the periodic table. More specifically, iron, cobalt, nickel, ruthenium, rhodium, palladium, osmium, iridium, and platinum can be suitably exemplified. A solid acid catalyst caused to carry platinum out of those metals is particularly preferable.

In addition, suitable examples of solid acids for carrying those metals include: various zeolites such as A-type zeolite, L-type zeolite, X-type zeolite, Y-type zeolite, and ZSM-5; and metal oxides such as silica alumina, alumina, and heteropoly acid. Of those solid acids, X-type zeolite and Y-type zeolite are particularly preferable.

In addition, a metal-carrying solid acid catalyst can be produced by causing zeolite described above serving as a carrier to carry at least one kind of the above metals by means of an ion exchange method or an impregnation method.

Here, when the catalyst is produced by means of an ion exchange method, the catalyst can be obtained by: bringing a metal salt of at least one kind of the above metals or an aqueous solution of a metal complex salt of at least one kind of the above metals into contact with zeolite; subjecting a cation site (such as $H^-$ or $NH^{4+}$) in zeolite to ion exchange; drying the resultant; and baking the resultant.

In addition, when the catalyst is produced by means of an impregnation method, the catalyst can be obtained by: mixing zeolite with the above metal salt or the above aqueous solution of a metal complex salt; evaporating the mixture to dryness by using a rotary evaporator or the like; and impregnating the resultant with the metal to cause the resultant to carry the metal. The catalyst thus obtained may be of either a powdery form or a granular form.

In addition, the form of a reactor to be used in the isomerization reaction is not particularly limited. For example, a so-called fixed bed continuous reactor which is filled with a catalyst and is continuously supplied with a starting material can be used, but a reactor that can be used is not limited to this. A reactor of any form which is of an ordinary solid-liquid contact type or solid-gas contact type can be used irrespective of whether the reactor follows a continuous mode or a batch mode.

TMN may be purified before it is used in the isomerization reaction, or may be directly used in the reaction without being purified. In each case, TMN can be used in combination with a solvent. The ratio of the solvent at this time is ordinarily about 0 to 10 parts by mass, or preferably 0 to 3 parts by mass with respect to 1 part by mass of TMN. When TMN is directly used without being purified, a solvent ratio can be adjusted to the above range by removing part of the solvent used in a hydrogenation step or by newly adding a solvent.

Conditions for the isomerization reaction include: a reaction temperature of ordinarily about 150 to 500° C., or preferably 200 to 400° C.; and a pressure of ordinarily normal pressure to about 20 MPa, or preferably 2 to 8 MPa. The reaction is preferably performed in the coexistence of hydrogen from the viewpoint of an increase in yield. In addition, a weight space velocity (WHSV) is ordinarily about $5.0\ h^{-1}$ or lower, or preferably 0.01 to $5.0\ h^{-1}$ from the viewpoint of an increase in TMN conversion ratio.

Furthermore, in the present invention, the isomerization reaction of TMN can be performed in coexistence with a monocyclic, saturated hydrocarbon compound, an aromatic compound, water, and/or any one of alcohols. Here, examples of the monocyclic, saturated hydrocarbon compound to be made to coexist include cyclopentane, cyclohexane, ethylcyclohexane, and methylcyclohexane. Cyclohexane or ethylcyclohexane, or a mixture of them is particularly suitable.

In addition, examples of the aromatic compound include: aromatic hydrocarbon compounds such as benzene, toluene, xylene, naphthalene, and anthracene; oxygen-containing aromatic compounds such as phenol, benzaldehyde, benzoic acid, benzyl alcohol, and anisole; nitrogen-containing aromatic compounds such as aniline and nitrobenzen; and halogen-containing aromatic compounds such as chlorbezene and bromobenzene.

Of those aromatic compounds, aromatic hydrocarbon compounds such as benzen, toluene, xylene, naphthalens, and anthracene are more preferable, and benzene is particularly preferable.

On the other hand, examples of alcohols include: monohydric alcohol such as methyl alcohol, isopropyl alcohol, tert-butyl alcohol, and benzyl alcohol, and polyhydric alcohol such as ethylene glycol and glycerin.

The addition amount of each of those compounds to be made to coexist is not particularly limited, and can be appropriately selected depending on various situations.

(B) Concentration Step

The concentration step is a step of subjecting a liquid reaction mixture as a result of the isomerization reaction obtained in the above isomerization step to a concentration treatment with a single flash column or distillation column, or a combination of multiple flash columns or distillation columns according to a batch mode or a continuous mode so that the solvent and a light by-product (impurity) are removed, and the liquid is concentrated up to such a concentration that the liquid can be efficiently crystallized in the subsequent crystallization step.

In the concentration step, an unreacted light gas such as hydrogen is removed by using a flash column, and concentration is completed by using one distillation column in ordinary cases. In addition, concentration is performed in such a manner that an adamantane concentration is ordinarily 10 to 50 mass %, or preferably 20 to 40 mass %. When the concentration ratio is excessively low, the recovery efficiency of adamantane in the crystallization step degrades. On the other hand, when the concentration ratio is excessively high, impurities are also relatively concentrated, so the impurities are apt to be taken in adamantane in the crystallization step.

In the present invention, a product having an APHA color of 5 or lower can be obtained by controlling the content of endo-trimethylenenorbornane (which may hereinafter be abbreviated as "endo-TMN") in the concentrate in such a manner that a ratio endo-TMN/adamantane (mass ratio) is 0.25 or lower, or preferably 0.20 or lower.

The above APHA color can be determined by: dissolving an adamantane crystal into tetrahydrofuran (THF) in such a manner that a ratio adamantane crystal/THF (mass ratio) equals 1/10; and measuring the absorbance of the solution with light having a wavelength of 375 nm. To be specific, the APHA color can be determined by: creating an analytical curve showing a relationship between an absorbance and an APHA color in advance by using an APHA standard solution; and converting a measured value into an APHA color. The analytical curve was created by: defining the APHA color of a "Chromaticity standard solution 1000 degrees" manufactured by Kishida Chemical Co., Ltd. as 1,000; diluting the standard solution with distilled water to n thousandths (volume fraction) to prepare a solution having an APHA color of n (n=1, 5, 10, 20, or 100); and measuring an absorbance at a wavelength of 375 nm.

Suppressing the content of endo-TMN in the concentrate to be used in the subsequent crystallization step can provide a product having an APHA color of 5 or lower because of the following reason. That is, the isomerization reaction of adamantane results in the production of an extremely large amount of a by-product, so it is difficult to specify a substance responsible for coloration. Since the APHA color of endo-TMN measured by means of the above method is 1, endo-TMN itself is not a coloring substance. However, when endo-TMN is taken in an adamantane crystal owing to a crystallization operation, a substance to be responsible for coloration is simultaneously apt to be taken in the adamantane crystal, so the substance becomes a factor for coloration. Suppressing the content of endo-TMN in a concentrate can provide a product having an APHA color of 5 or lower.

(C) Crystallization Step

The crystallization step is a step of crystallizing adamantane from the concentrate obtained in the above concentration step according to a batch mode or a continuous mode.

General cooling crystallization or evaporation crystallization, or a combination of them can be employed as a crystallization operation. An operation temperature in the crystallization operation depends on the adamantane concentration of the concentrate. In the case of continuous crystallization, the operation temperature is ordinarily about −20 to 50° C., or preferably 0 to 30° C. When the temperature is −20° C. or higher, energy consumption upon cooling can be suppressed. When the temperature is 50° C. or lower, the solubility of adamantane in a solvent is so low that the recovery efficiency of adamantane increases. In addition, in any other crystallization method, it is advantageous to define the temperature at which the solubility of adamantane is about 0.5 to 25 mass %, or preferably 5 to 15 mass % as the final temperature in the crystallization step because of the same reason.

When an impurity causing a problem in terms of quality is taken in by one crystallization, recrystallization may be performed immediately after the crystallization. Alternatively, after a solid-liquid separation step and a washing step as post-processing steps, the recrystallization, the solid-liquid separation step, and the washing step may be repeated multiple times.

(D) Solid-Liquid Separation Step

The solid-liquid separation step is a step of separating the adamantane crystals crystallized in the crystallization step and the solvent from slurry resulting from the crystallization according to a batch mode or a continuous mode.

A general method involving the use of filter cloth, a sintered metal, or the like can be employed as a solid-liquid separation operation.

The degree of solid-liquid separation is desirably such that a liquid content in a separated crystal cake is about 50 mass % or lower, or preferably 5 to 30 mass %.

A product having a target purity can be efficiently obtained by appropriately adjusting the amount of a mother liquor to be discharged to the outside of a system and the amount of the mother liquor to be recirculated depending on, for example, the concentration of adamantane or any other impurity in the mother liquor, or a flow rate balance in a process.

(E) Washing Step

The washing step is a step of washing and removing the solvent that cannot have been sufficiently removed in the above solid-liquid separation by using a washing solvent.

Any one of most organic solvents can be used as the washing solvent; provided that, in consideration of the ease of a treatment in a drying step as a subsequent step, a low-boiling solvent that can be easily dried is preferable, and a solvent having a boiling point of 150° C. or lower is suitable in ordinary cases. Examples of such solvent include methyl alcohol, ethyl alcohol, n-propyl alcohol, isopropyl alcohol, acetone, methyl ethyl ketone, diethyl ketone, acetic acid, carbon tetrachloride, pentane, hexane, cyclohexane, ethylcyclohexane, benzene, toluene, and xylene. In particular, a middle distillate fraction having a boiling point of 150° C. or lower obtained as a result of petroleum refining or obtained from a petrochemical factory is inexpensive and optimum.

A washing operation temperature is in the range of ordinarily room temperature to a temperature equal to or lower than the boiling point of the washing solvent, or preferably −20 to 50° C.

(F) Drying Step

The drying step is a step of subjecting the washed adamantane crystals obtained in the above washing step to a drying treatment.

A general drying machine that has been industrially used such as a vacuum drying machine or a heated drying machine can be used in the drying treatment. In addition, a drying method may follow either a continuous mode or a batch mode.

Since the object of the drying treatment lies in the removal of a washing solvent, operating conditions for the treatment vary depending on the kind of a solvent to be used in the washing step; provided that, in ordinary cases, a pressure is equal to or lower than normal pressure, or preferably 5 to 101 kPa, and a temperature is equal to or lower than the boiling point of the washing solvent, or preferably 20 to 60° C.

Thus, the need for a troublesome operation such as waste liquid disposal is eliminated, and high-purity adamantane reduced in coloration can be efficiently produced while minimizing the loss.

EXAMPLES

Next, the present invention will be described in more detail by way of examples. However, the present invention is not limited by these examples at all.

Preparation Example 1

Preparation of Metal-Carrying Solid Acid Catalyst 235 g of Y-type zeolite subjected to sodium ion exchange were suspended into 2,000 g of pure water under stirring, and the suspension was added with a dilute aqueous solution of nitric acid, whereby the pH of suspension slurry was adjusted to 5.5. Next, a solution prepared by dissolving 246 g of lanthanum nitrate hexahydrate into 500 g of hot water was gradually mixed with the above suspension slurry.

After that, the temperature of the mixture was heated to 90° C., and the mixture was stirred for 30 minutes, followed by filtration and washing. Next, a washed cake was subjected to a drying treatment at 110° C. overnight, and the resultant was baked at 600° C. for 3 hours. Slurry prepared by suspending the baked powder into 2,000 g of pure water again under stirring was added with 228 g of ammonium sulphate, and the whole was stirred at 95° C. for 30 minutes, followed by filtration and washing. The washed cake was suspended into 2,000 g of water again, and a similar ion exchange operation was performed twice continuously.

After that, the resultant was subjected to a drying treatment at 110° C. overnight. Then, the resultant was loaded into a tubular container, and the whole was subjected to steaming in 100% water vapor at 510° C. for 30 minutes. Next, the resultant powder was suspended into 2,000 g of pure water, and 32 g of 25-mass % sulfuric acid were gradually added to the suspension, followed by heating at 95° C. for 30 minutes.

After that, the resultant was subjected to filtration and washing, and was then suspended into 2,000 g of pure water again. 180 g of a 1.71-mass % aqueous solution of tetraammine platinum chloride were added to the suspension, and the whole was stirred at 60° C. for 30 minutes. After having been subjected to filtration and washing, the resultant was subjected to a drying treatment at 110° C. overnight, whereby a catalyst composed of La-containing Y-type zeolite carrying 0.87 mass % of platinum owing to ion exchange was obtained.

Example 1

(1) Reaction-Concentration Step

A reaction tube made of stainless steel was filled with 20 g of the catalyst obtained in Preparation Example 1, and the catalyst was baked in a stream of the air at 300° C. for 3 hours. After having been replaced with nitrogen, the resultant was subjected to hydrogen reduction at normal pressure in a stream of hydrogen at 300° C. for 2 hours. After that, the supply of a 78-mass % solution prepared by dissolving TMN into decalin and hydrogen was initiated, and an isomerization reaction was continuously performed under the conditions of 300° C., 5 MPa, WHSV=2.4 h$^{-1}$, and hydrogen/ TMN (molar ratio)=2. The reaction results were as follows: a TMN conversion ratio of 82% and an adamantane yield of 11%.

A liquid reaction mixture was concentrated by means of 15-stage atmospheric distillation at a column bottom temperature of 180° C. until an adamantane concentration became 30.0 mass %. The concentrate contained 49.1 mass % of unreacted TMN (endo-TMN=0.4 mass %, exo-TMN=48.7 mass %) and 16.0 mass % of a by-product.

(2) Purification Step 300 g of the concentrate obtained in the above step (1) to serve as a crystallization material were loaded into a flask, and were stirred and dissolved at 120° C. The ratio endo-TMN/adamantane (mass ratio) at this time was 0.01. While stirring was continued, the temperature of the resultant was slowly cooled to 10° C. for crystallization, whereby slurry in which adamantane was precipitated was obtained. Next, the slurry was filtered through a 70-µm glass filter. The resultant adamantane crystal contained 15 mass % of unreacted TMN and 5 mass % of a by-product. 75 g of the adamantane crystal were added with 75 g of isopropyl alcohol on the 70-µm glass filter, and the whole was subjected to replacing washing by means of suction filtration.

Isopropyl alcohol was evaporated from the crystal after the washing through air-drying, whereby 59 g of a crystal after the drying were obtained. The analysis of the crystal by means of gas chromatography confirmed that adamantane having a TMN content of 1 mass %, a by-product content of 1 mass %, and a purity of 98 mass % was obtained.

The coloration of the resultant adamantane crystal was measured as described below. That is, the adamantane crystal was dissolved into tetrahydrofuran (THF) in such a manner that a ratio adamantane crystal/THF (mass ratio) would equal 1/10, and the absorbance of the solution was measured with light having a wavelength of 375 nm. An analytical curve showing a relationship between an absorbance and an APHA color was created in advance by using an APHA standard solution, and a measured value was converted into an APHA color. As a result, the crystal had an APHA color of 1.

Example 2

(1) Reaction-Concentration Step

An isomerization reaction was performed in the same manner as in Example (1) except that a WHSV was changed to 4.8 h$^{-1}$ in the step (1) of Example 1. The reaction results were as follows: a TMN conversion ratio of 60% and an adamantane yield of 8%.

A liquid reaction mixture was concentrated by means of 15-stage atmospheric distillation at a column bottom temperature of 180° C. until an adamantane concentration became 30.0 mass %. The concentrate contained 53.7 mass % of unreacted TMN (endo-TMN=6.0 mass %, exo-TMN=47.7 mass %) and 11.2 mass % of a by-product.

(2) Purification Step 300 g of the concentrate obtained in the above step (1) to serve as a crystallization material were loaded into a flask, and were stirred and dissolved at 120° C. The ratio endo-TMN/adamantane (mass ratio) at this time was 0.2. While stirring was continued, the temperature of the resultant was slowly cooled to 10° C. for crystallization, whereby slurry in which adamantane was precipitated was obtained. Next, the slurry was filtered through a 70-µm glass filter. The resultant adamantane crystal contained 18 mass % of unreacted TMN and 2 mass % of a by-product. 75 g of the adamantane crystal were added with 75 g of isopropyl alcohol on the 70-μm glass filter, and the whole was subjected to replacing washing by means of suction filtration.

Isopropyl alcohol was evaporated from the crystal after the washing through air-drying, whereby 59 g of a crystal after the drying were obtained. The analysis of the crystal by means of gas chromatography confirmed that adamantane having a TMN content of 3 mass %, a by-product content of 1 mass %, and a purity of 96 mass % was obtained.

The coloration of the resultant adamantane crystal was measured in the same manner as in the step (2) of Example 1. As a result, the crystal had an APHA color of 5.

Comparative Example 1

(1) Reaction-Concentration Step

An isomerization reaction was performed in the same manner as in Example (1) except that a WHSV was changed to 6.0 $h^{-1}$ in the step (1) of Example 1. The reaction results were as follows: a TMN conversion ratio of 40% and an adamantane yield of 6%.

A liquid reaction mixture was concentrated by means of 15-stage atmospheric distillation at a column bottom temperature of 180° C. until an adamantane concentration became 30.0 mass %. The concentrate contained 52.5 mass % of unreacted TMN (endo-TMN=24.4 mass %, exo-TMN=28.1 mass %) and 13.1 mass % of a by-product.

(2) Purification Step 300 g of the concentrate obtained in the above step (1) to serve as a crystallization material were loaded into a flask, and were stirred and dissolved at 120° C. The ratio endo-TMN/adamantane (mass ratio) at this time was 0.81. While stirring was continued, the temperature of the resultant was slowly cooled to 10° C. for crystallization, whereby slurry in which adamantane was precipitated was obtained. Next, the slurry was filtered through a 70-μm glass filter. The resultant adamantane crystal contained 18 mass % of unreacted TMN and 2 mass % of a by-product. 75 g of the adamantane crystal were added with 75 g of isopropyl alcohol on the 70-μm glass filter, and the whole was subjected to replacing washing by means of suction filtration.

Isopropyl alcohol was evaporated from the crystal after the washing through air-drying, whereby 59 g of a crystal after the drying were obtained. The analysis of the crystal by means of gas chromatography confirmed that adamantane having a TMN content of 7 mass %, a by-product content of 1 mass %, and a purity of 92 mass % was obtained.

The coloration of the resultant adamantane crystal was measured in the same manner as in the step (2) of Example 1. As a result, the crystal had an APHA color of 9.

Comparative Example 2

The concentrate obtained in the step (1) of Example 1 was added with endo-TMN and adamantane, whereby a liquid having an adamantane concentration of 30.0 mass %, a TMN concentration of 56.3 mass % (endo-TMN=24.3 mass %, exo-TMN=32.0 mass %), and a by-product concentration of 10.5 mass % was prepared.

300 g of the prepared liquid to serve as a crystallization material were loaded into a flask, and were stirred and dissolved at 120° C. The ratio endo-TMN/adamantane (mass ratio) at this time was 0.81. While stirring was continued, the temperature of the resultant was slowly cooled to 10° C. for crystallization, whereby slurry in which adamantane was precipitated was obtained. Next, the slurry was filtered through a 70-μm glass filter. The resultant adamantane crystal contained 18 mass % of unreacted TMN and 2 mass % of a by-product. 75 g of the adamantane crystal were added with 75 g of isopropyl alcohol on the 70-μm glass filter, and the whole was subjected to replacing washing by means of suction filtration.

Isopropyl alcohol was evaporated from the crystal after the washing through air-drying, whereby 59 g of a crystal after the drying were obtained. The analysis of the crystal by means of gas chromatography confirmed that adamantane having a TMN content of 7 mass %, a by-product content of 1 mass %, and a purity of 92 mass % was obtained.

The coloration of the resultant adamantane crystal was measured in the same manner as in the step (2) of Example 1. As a result, the crystal had an APHA color of 9.

Example 3

(1) Reaction-Concentration Step 500 g of anhydrous aluminum chloride and 650 mL of 1,2-dichloroethane were loaded into a reaction vessel, and the whole was stirred. After that, a solution prepared by dissolving 1,400 g of endo-TMN into 700 mL of 1,2-dichloroethane was slowly dropped to the resultant under ice cooling, and then the whole was heated and stirred at 60° C. for 2 hours, whereby an isomerization reaction was performed. The reaction results were as follows: a TMN conversion ratio of 30% and an adamantane yield of 15%. After the completion of the reaction, 1,2-dichloroethane was distilled off at 14.7 kPa and 60° C.

The residue after distillation was subjected to an extraction treatment with hexane. Subsequently, a hexane extract was concentrated by means of 15-stage atmospheric distillation at a column bottom temperature of 180° C. until an adamantane concentration became 30.0 mass %. The concentrate contained 70.1 mass % of unreacted TMN (endo-TMN=0.5 mass %, exo-TMN=69.6 mass %) and 0 mass % of a by-product.

(2) Purification Step 300 g of the concentrate obtained in the above step (1) to serve as a crystallization material were loaded into a flask, and were stirred and dissolved at 120° C. The ratio endo-TMN/adamantane (mass ratio) at this time was 0.02. While stirring was continued, the temperature of the resultant was slowly cooled to 10° C. for crystallization, whereby slurry in which adamantane was precipitated was obtained. Next, the slurry was filtered through a 70-μm glass filter. The resultant adamantane crystal contained 15 mass % of unreacted TMN and 5 mass % of a by-product. 75 g of the adamantane crystal were added with 75 g of isopropyl alcohol on the 70-μm glass filter, and the whole was subjected to replacing washing by means of suction filtration.

Isopropyl alcohol was evaporated from the crystal after the washing through air-drying, whereby 59 g of a crystal after the drying were obtained. The analysis of the crystal by means of gas chromatography confirmed that adamantane having a TMN content of 1 mass %, a by-product content of 1 mass %, and a purity of 98 mass % was obtained.

The coloration of the resultant adamantane crystal was measured in the same manner as in the step (2) of Example 1. As a result, the crystal had an APHA color of 1.

Comparative Example 3

The concentrate obtained in the step (1) of Example 3 was added with endo-TMN and adamantane, whereby a liquid having an adamantane concentration of 29.9 mass %, a TMN concentration of 70.1 mass % (endo-TMN=24.3 mass %, exo-TMN=45.8 mass %), and a by-product concentration of 0 mass % was prepared.

300 g of the prepared liquid to serve as a crystallization material were loaded into a flask, and were stirred and dissolved at 120° C. The ratio endo-TMN/adamantane (mass ratio) at this time was 0.81. While stirring was continued, the temperature of the resultant was slowly cooled to 10° C. for crystallization, whereby slurry in which adamantane was precipitated was obtained. Next, the slurry was filtered through a 70-μm glass filter. The resultant adamantane crystal contained 18 mass % of unreacted TMN and 2 mass % of a by-product. 75 g of the adamantane crystal were added with 75 g of isopropyl alcohol on the 70-μm glass filter, and the whole was subjected to replacing washing by means of suction filtration.

Isopropyl alcohol was evaporated from the crystal after the washing through air-drying, whereby 59 g of a crystal after the drying were obtained. The analysis of the crystal by means of gas chromatography confirmed that adamantane having a TMN content of 7 mass %, a by-product content of 1 mass %, and a purity of 92 mass % was obtained.

The coloration of the resultant adamantane crystal was measured in the same manner as in the step (2) of Example 1. As a result, the crystal had an APHA color of 9.

The invention claimed is:

1. A process for producing adamantane having an APHA color of 5 or lower by isomerizing trimethylenenorbornane, the process comprising:
   (A) isomerizing trimethylenenorbornane to produce a resultant liquid reaction mixture comprising adamantane;
   (B) concentrating adamantane contained in the resultant liquid reaction mixture until the adamantane concentration is 10 to 50 mass %;
   (C) precipitating the adamantane concentrated in the resultant liquid via crystallization at an operating temperature of about −20 to 50° C. and finally at a temperature at which the solubility of adamantane is about 0.5 to 25 mass % provide a slurry;
   (D) separating adamantane crystals from the slurry to provide isolated adamantane crystals wherein the degree of solid-liquid separation is such that a liquid content in a separated crystal cake is about 50 mass %;
   (E) washing the isolated adamantane crystals at a temperature of −20 to 50° C. using a solvent having a boiling point of 150° C. or lower; and
   (F) drying the washed adamantane crystals at a pressure of 5 to 101 kPa and a temperature of 20 to 60° C.,
   wherein a mass ratio of endo-trimethylenenorbornane to adamantane contained in materials subjected to step (C) (endo-trimethylenenorbornane/adamantane) is 0.25 or lower and wherein the washed adamantane crystals have an APHA color of 5 or lower.

2. A process for producing adamantane according to claim 1, wherein a solid catalyst is used in isomerizing the trimethylenenorbornane.

3. A process for producing adamantane according to claim 2, wherein the solid catalyst is a metal-carrying solid acid catalyst.

4. A process for producing adamantane according to claim 2, wherein the solid catalyst comprises aluminum chloride.

5. A process for producing adamantane according to claim 3, wherein the metal in the metal-carrying solid acid catalyst is selected from the group consisting of metals belonging to Groups 8 to 10 of the periodic table.

6. A process for producing adamantane according to claim 3, wherein the metal in the metal-carrying solid acid catalyst is selected from the group consisting of iron, cobalt, nickel, ruthenium, rhodium, palladium, osmium, iridium, and platinum.

7. A process for producing adamantane according to claim 1, wherein the (A) isomerization is conducted in a fixed bed continuous reactor which is filled with a catalyst and is continuously supplied with trimethylenenorbornane.

8. A process for producing adamantane according to claim 1, wherein the (A) isomerization is conducted at a reaction temperature of about 150 to 500° C. and a pressure of normal pressure to about 20 MPa, optionally in the presence of hydrogen.

9. A process for producing adamantane according to claim 1, wherein the (A) isomerization is conducted in the presence of at least one compound selected from the group consisting of a monocyclic, saturated hydrocarbon compound, an aromatic compound, water, and an alcohol.

10. A process for producing adamantane according to claim 1, wherein the (A) isomerization is conducted in the presence of at least one compound selected from the group consisting of cyclopentane, cyclohexane, ethylcyclohexane, methylcyclohexane, benzene, toluene, xylene, naphthalene, anthracene, phenol, benzaldehyde, benzoic acid, benzyl alcohol, anisole, aniline, nitrobenzene, chlorbenzene , bromobenzene, methyl alcohol, isopropyl alcohol, tert-butyl alcohol, benzyl alcohol, ethylene glycol and glycerin.

* * * * *